US006841177B1

(12) United States Patent
Quintanilla Almagro et al.

(10) Patent No.: US 6,841,177 B1
(45) Date of Patent: Jan. 11, 2005

(54) PHARMACOLOGICAL ACTIVITIES OF CURCUMA LONGA EXTRACTS

(75) Inventors: Elisso Quintanilla Almagro, Alicante (ES); Ana Ramírez Bosca, Alicante (ES); August Bernd, Alicante (ES); José Pardo Zapata, Alicante (ES); Joaquin Diaz Alperi, Alicante (ES); David Pamies Mira, Alicante (ES); Miguel Angel Carrion Gutierrez, Alicante (ES); José Miguel Sempere Ortells, Alicante (ES)

(73) Assignee: ASAC Compania de Biotecnologia e Investigacion S.A., Alicante (ES)

( * ) Notice: Subject to any disclaimer, the term of this patent is extended or adjusted under 35 U.S.C. 154(b) by 190 days.

(21) Appl. No.: 09/856,035

(22) PCT Filed: Sep. 21, 2000

(86) PCT No.: PCT/ES00/00354

§ 371 (c)(1),
(2), (4) Date: Feb. 19, 2002

(87) PCT Pub. No.: WO01/21185

PCT Pub. Date: Mar. 29, 2001

(30) Foreign Application Priority Data

Sep. 23, 1999 (ES) .............................................. 9902364

(51) Int. Cl.$^7$ ............................................... A61K 35/78
(52) U.S. Cl. ........................ 424/756; 514/824; 514/863
(58) Field of Search ......................... 424/756; 514/824, 514/863

(56) References Cited

U.S. PATENT DOCUMENTS

| 5,401,777 A | | 3/1995 | Ammon |
| 5,891,924 A | * | 4/1999 | Aggarwal |
| 6,019,735 A | * | 2/2000 | Kensey et al. |
| 6,440,468 B1 | * | 8/2002 | Quintanilla Almagro et al. |
| 2002/0164374 A1 | * | 11/2002 | Jackson et al. |

OTHER PUBLICATIONS

Bosca et al. Age. 1997. vol. 20, No. 3, pp. 165–168.*
Deshpande et al. Medical Science Research. 1997. vol. 25, No. 10, pp. 695–698.*
Quiles et al. BioFactors. 1998. vol. 8 (1–2), pp. 51–57.*
Tsuda et al. Atherosclerosis. 1996. vol. 122, No. 2, pp. 225–233.*
Miquel et al, *Age, 18(4)* : 171–174 (1995).
Srinivas et al, *Archives of Biochem. and Biophys., 292(2)* : 617–623 (1992).
Dahl et al, *Photochem. and Photobiol., 59(3)* :290–294 (1994).
Ishizaki et al, *Dermatology, 193(4)* :311–317 (1996).
Huang et al, *Eru. J. of Pharmacology, 221*:381–384 (1992).
Simon et al, *Cancer Letters, 129(1)* :111–116 (1998).
Yasni et al, *Food Chem. Toxic., 31(3)* :213–218 (1993).

* cited by examiner

Primary Examiner—Christopher R. Tate
(74) Attorney, Agent, or Firm—Sughrue Mion, PLLC (57) ABSTRACT

New pharmacological activities of *Curcuma Longa* extracts as antiproliferative and photosensitivisation agents and their use in proliferative diseases such as psoriasis, as reducers of plasmatic fibrinogen and the Apolipoprotein B/Apolipoprotein A-I quotient, without altering other coagulation parameters.

10 Claims, 8 Drawing Sheets

PHARMACOLOGICAL ACTIVITIES OF CURCUMA LONGA EXTRACTS

This application is a § 371 of PCT/ES00/00354, filed Sep. 21, 2000.

TECHNICAL FIELD OF THE INVENTION

This invention describes the new pharmacological activities of *Curcuma longa* extracts as an antiproliferative agent with an effect similar to betamethasone-17-valerate and a photosensitivisation effect greater than psoralens and its use in a pharmaceutical composition as an agent in proliferative diseases such as psoriasis, mycosis fungoides, atopic dermatitis, and photodermatosis without the side effects caused by psoralens, corticoids and/or retinoids. The photosensitivisation effect is active both with ultraviolet light and visible light.

This invention refers to a new pharmacological effect of *Curcuma* extracts as an antiatheromatous agent, reducing plasmatic fibrinogen and the apolipoprotein B/apolipoprotein A-I quotient, without altering the other coagulation parameters.

State of the Art

Psoriasis is a chronic inflammatory dermatitis of unknown aetiology. Clinically, it is characterized by papulous lesions on erythemato-scaly maculae. The majority of these lesions are due to alterations in cellular proliferation marked by immunological and genetic mechanisms.

We find an increase in arachinonic acid and its derivatives, both in normal and diseased skin; an increase in polyamines, an increase of B4 leukotriene in the scales. From the epidermis and the dermis we find an increase in Langerhans cells with lower infiltration of CD8 lymphocytes compared with CD4. These patients' neutrophils synthesize double the number of B4 leukotrienes as healthy individuals. IL-6 interleukin is a cytokine that structures the 2(BSF-2) factor, structurally identical to interferon $\beta$-2 (IFN-$\beta$-2). IL-6 is synthesized in the fibroblasts, monocytes and T cells. This cytokine stimulates the acute phase of protein synthesis and the production of immunoglobulins.

IL-8 is an interleukin that is directly involved in psoriasis, since it is responsible for producing the migration of the neutrophils that are produced in the epidermis and consequently increases the inflammatory process.

In the present therapy used for psoriasis it is fundamental to act on cellular proliferation and the production of cytokines by the use of glucocorticoids and/or photosensitivisation agents (psoralens).

Cell cultures are acknowledged models for the study of cell physiology and the effect of drugs. HaCat cells are derived from human keratinocytes that exhibit the same differentiations as normal keratinocytes. Therefore, HaCat cells are an extraordinary model for testing different substances for topical application.

Keratinocytes are very biologically active cells, the function of which is not only to produce keratin synthesis to form the corneal stratus, but which also have immunological properties based on the production and secretion of cytokines and the selective expression of surface receivers.

Different stimulants including ultraviolet radiation have inflammatory responses that act directly on these keratinocytes, producing a release of cytokines and adhesion molecules. This production of substances on the epidermis level starts the cutaneous inflammation symptoms, releasing the IL-6 and the IL-8, which are two cytokines involved in inflammatory cutaneous processes.

Glucocorticoids are the substances most used in the dermatology field, because of their immunosuppressant and anti-inflammatory properties, manifest after UV radiation, but with no effect in visible light.

Different studies show that corticoids affect the production of pro-inflammatory cytokines. Well known glucocorticoids such as hydrocortisone-17-butyrate and betametasone-17-valerate produce a decrease in inflammatory cytokines after ultra-violet radiation.

The accessibility of the skin often allows for skin alterations to be treated by the topical application of drugs. Topical corticoids, thanks to their anti-inflammatory, vaso constricting and antimycotic properties, have been seen to be useful in a large variety of dermatosis. Nevertheless, the application of corticoids has a series of side effects that have a direct impact on the skin:

Cutaneous atrophies, which consist of thin, transparent skin, purple lesions, star-shaped scars and elastic catabolic striae.

Delay in scar formation because of inhibition of the fibroblasts' function.

Disguise and de-typing of cutaneous infections, particularly dermatophytosis, making diagnosis difficult and with the possible appearance of viral or bacterial cutaneous infections.

Skin pigmentation disorders with hyper or hypopigmentation.

Contact dermatitis.

Habituation and tachyphylaxis phenomena that require the use of increasingly strong products and lead to relapses with the appearance of increasingly severe forms of the process (pustular psoriasis) that could be caused by suddenly ceasing administration.

Systemic side effects are fortunately less frequent, since the use of corticoids for long periods is required, as for psoriasis. The most common side effects are:

Inhibition of the hypothalamus—hypophysial—suprarenal axis.

Episodes of hyperglucaemia and glucaemia.

A fall in the number of eosinophils.

Clinical manifestations of Cushing's Syndrome.

Other therapies used for psoriasis are the oral or topical application of photosensitivisation substances (psoralens) together with ultraviolet A radiation. The photochemistry of psoralens is not well know, and can act on several levels. Psoralens bind with DNA and RNA, but interact with lysosomes, endotheliums, cytoplasmatic membranes and dermic cells. In the dark, psoralen is intercalated between the DNA bases. With UVA, cyclobutane monoadducts are produced by binding with a DNA base thymine or cytokine. If radiation continues, a new photon stimulates the other double psoralen link to form a crossover link with the thymine from the other DNA chain. The formation of these bifunctional adducts suppresses DNA synthesis. Another reaction that is observed is that the photoactivated psoralen can act with molecular oxygen to produce an oxygen singlet, superoxide anion and free radicals, and all these reactive forms act on the keratinocytes. The use of psoralens, therefore, presents side effects that are well known in dermatological literature, such as a decrease in delayed immunity, phototoxic reactions, immunosuppression, a decrease in the production of IL-1 by the keratinocytes and more inclination to skin cancers.

On the other hand, photosensitivisation substances can be used in the treatment of different diseases with an excess of hyperproliferation such as vitiligo, atopic dermatitis, granuloma annulare, lichen, mycosis fungoides, lymphomas, leukaemia, etc.

One of the greatest coronary risk factors is the plasmatic concentration of fibrinogen. Stone and Thorp *J. Royal College Gen Practitioners* 35,565–569 (1985), showed that in men between 40–60 years of age there is a relation between heart attacks and the plasmatic levels of fibrinogen. Particularly in men with high cholesterol and high arterial pressure, heart attack frequency was 6 and 12 times greater, respectively, in individuals with high levels of fibrinogen compared with individuals with low fibrinogen levels. In multivariable models, then, fibrinogen concentration is at least as important as other risk factors for cardiac diseases, such as cholesterol, smoking and arterial pressure. Another demonstration of the pathogenetic role of fibrinogen and its products has been described by Kaplan and Bini. *Arteriosclerosis* 9, 109 (1989). They conclude that fibrinogen is involved in atheroma plaques. The study of atheroma plaques by anti-body fluorescence (with antifibrinogen polyclonal anti-bodies) shows fibrinogen or fibrin in a wide range of atherosclerotic lesions.

Sadoshima and Tanaka. *Atherosclerosis* 34, 93–97 (1979) have also shown an accumulation of fibrinogen and LDL in human cerebral arteries. In early atheroma plaques fibrinogen is observed in the interstices of the intima and between the duplicated internal elastic laminae. The authors describe the accumulation of fibrinogen in the intima before the LDL and therefore fibrinogen is a greater risk factor than LDL.

Consequently, a drug capable of reducing the plasmatic concentration of fibrinogen would be useful for the treatment and/or prophylaxis of cardiovascular diseases.

The drugs used as fibrinogen reducers (salicylic acid, cumarin derivatives) increase fibrinolytic activity, and have side effects on coagulation parameters (Quick's index, thrombin time, prothrombin time, ATPP).

Apolipoprotein B is the fundamental protein component of low density lipoproteins (LDL), so that high concentrations of this protein indicate a large amount of LDL. It is known that this lipoprotein, when it oxidises, is captured by the macrophages and its transformation into foam cells is determinant for the start of atheroma plaques. The more apolipoprotein B there is in plasma, then, the greater the risk of atheroma.

Apolipoprotein A-I is a fundamental particle component in high density lipoproteins (HDL). Its function is to activate the lecithin-cholesterol-acyl-transferase enzyme, in charge of forming cholesterol esters from the free cholesterol from the peripheral tissues and the phospholipids that form the HDL particle itself. These lipoproteins are fundamental for the maintenance of cholesterol homeostasis, since the remove the cholesterol accumulated in the peripheral tissues and they take it to the liver, where it is eliminated as biliary salts or recirculated to other lipoproteins. High concentrations of Apo A-I, therefore, indicate less risk of atheroma.

The Apo B/Apo A-I ratio is therefore a better indicator of risk of atheroma, since the direction of the changes in atherosclerosis processes usually give rise to an increase of Apo B and a decrease of Apo A-I.

Curcumin and the curcuminoids present in the rhizomes of *Curcuma longa* and the Zingiberaceae family in general, have been used for the treatment of a large variety of diseases. Examples are U.S. Pat. No. 5,891,924 (inhibitor of NF kappa B activation), U.S. Pat. No. 5,336,496 (inhibitor of delta 5 desaturase), EP 256353 (treatment of bad absorption syndromes), EP 568001 (anti-viral agent), U.S. Pat. No. 5,108,750 (hyperlipidaemia and platelet aggregation reducer), FR 2655054 (cell protector) and EP 550807 (antioxidant and anti-inflammatory properties), EP440885 (anti-inflammatory), EP 319058 (against hair loss), U.S. Pat. No. 510,750, U.S. Pat. No. 4,906,471 and U.S. Pat. No. 4,842,859 (anti-platelet aggregation and anti-cholesterol agent), WO 88/05304 (treatment of neurological disorders), W 96/03999 (lipidic peroxide reducer), ES 20103689 (modulates high and low density oxidised lipoproteins, protects keratinocytes against free radicals and increases cell proliferation in aged human tissue). Chinese patent CN1156601 describes the use of medicinal composition prepared from 13 plants, including *Curcuma longa*, as a reducing agent for triglycerides and cholesterol increasing the HDL.

There is a large number of documents in the scientific literature, describing different pharmacological activities such as anti-tumour agent, anti-inflammatory, scar forming, proliferation inhibitor, anti-fungal, etc.

The aqueous extract of *Curcuma longa*, free from curcuminoids, has also been seen to have antioxidant properties. Srinivas et al. *Archives of Biochemistry and Biophysics* 292 n°2 617–623 (1992), describe the antioxidant activity of turmerin, a protein that is present in *Curcuma* rhizomes. Yeharayou et al *Ind J. Med. Res.* 64, 4, 601 (1976), describe the anti-inflammatory effect of the aqueous extract of *Curcuma longa*, with properties similar to hydrocortisone. Gonda et al. *Chem Pharm Bull* 40, 990 (1992) describe the immunological activity of ukonan A and its degradation products.

The document that is closes to our invention, Tonnessen et al *J. Pharm Sci* 76, n°5 (1987), describes the phototoxic activity of curcumin in coreless biological systems (*E. Coli, Salmonella typhimuis*); however, this document comments on the possible mutagenic effects on DNA.

Dhal et al *Photochemistry and Photobiology* 59 n°3, 290 (1994) describe the phototoxic activity of curcumin on rat cells.

None of the documents of the state of the art describes the photosensitivisation properties of aqueous *Curcuma longa* extracts, the inhibition of the secretion of inflammatory cytokines after UVA and/or visible radiation with aqueous *Curcuma longa* extracts and/or the beneficial effects on a clinical and histological level of a pharmaceutical composition the active ingredient of which is the aqueous *Curcuma longa* extract for different types of psoriasis with oral and topical application.

The development of this new pharmacological activity of *Curcuma longa* extract means that it is an ideal drug for the treatment of diseased with cell hyperproliferation such as psoriasis, without the side effects of the presently used treatments (psoralens, corticoids). Moreover, the photosensitivisation properties of *Curcuma* extracts with visible lights avoids the possible mutagenic effects of ultraviolet A or B radiation.

Neither does the state of the art describe the activity of *Curcuma longa* extracts as reducers of fibrinogen and the Apolipoprotein B/Apolipoprotein A-I quotient. The development of this new pharmacological activity of *Curcuma longa* extract means that it is an ideal drug for the treatment of atherosclerosis and cardiovascular diseases, without altering coagulation parameters.

The documents that are closest to our invention describe the lipidic peroxide reducing effect and the cholesterol reducing effect. These are etiopathogenic factors of the atherosclerotic process. However, these factors are unrelated.

Vitamin C and vitamin E, drugs that gave anti-oxidant and lipidic peroxide reducing properties, have had no effect on the plasmatic concentration of fibrinogen in humans after their administration. (Bates et al *J Hypertens*. July; 16 (7):

925–32 (1998)). Moghadasian et al *Circulation* April 6; 99 (13): 1733–1739 (1999) conclude that the probucol, which is known to have hypolipemiant and antioxidant capacity, increases the plasmatic concentrations of fibrinogen, showing proatherogenic activity. Rifici et al *Thromb Haemost* September; 78 (3): 1111–4 (1997) show that the lipooxidation produced by antioxidant vitamins does not alter the fibrinolitic activity.

The use of the vegetable extracts of plants with pharmacological activities is well known, and it is also known that the active ingredients can be isolated and purified from plant extracts. However, active ingredients that are purified and/or synthetically obtained could have side effects or be toxic, such as in the case of atropine, digitalis, nicotine etc.

Vegetable extracts contain a series of structurally related chemical species due to the metabolic processes in plants. These related compounds can have a synergic effect on pharmacological activity. These chemical substances are used as markers, in order to qualitatively and quantitatively standardize the extracts. The alcoholic extracts of *Curcuma* are chemically characterized in that they contain curcuminoids (curcumin, demethoxycurcumin and bidemethoxycurcumin). The aqueous extract of *Curcuma* is characterized in that it does not contain curcuminoids, but a protein fraction and a polysaccharide fraction, in which ukonan A, B and C have been identified. The pharmacological effect is due to the total composition of the aqueous and/or alcoholic extract of Curcuma longa.

Purpose of the Invention

This invention develops a new therapeutic application of the aqueous extract of *Curcuma longa* as a photosensitivisation agent, an antiproliferative agent and for use in diseases with an excess of cell proliferation, both with ultraviolet and visible light.

This invention develops a new therapeutic application of *Curcuma longa* extracts as a reducer of the plasmatic levels of fibrinogen, lowering them to normal values in healthy individuals and reducing the apolipoprotein B/apolipoprotein A quotient.

DETAILED DESCRIPTION OF THE INVENTION

The alcoholic extract of *Curcuma longa* can be obtained, according to Spanish patent ES 2103689, by the extraction of the *Curcuma* rhizomes by macerating with alcohol (methanol, ethanol) at 50° C. for 24 hours and then removing the solvent at reduced pressure. The alcoholic extract of *Curcuma longa* is chemically characterized in that it contains curcuminoids. Alternatively, other extraction and/or purification methods known by an expert can be used, such as extraction with other organic solvents, extraction with solvents in a supercritical state, reflux extraction and steam current extraction. The extract can be purified by fractioned crystallisation, chromatography, liquid—liquid extraction, etc.

The aqueous extract of *Curcuma* can also be obtained by macerating with water for 24 hours at 50–70° C. and then removing the solvent at reduced pressure. The aqueous extract of *Curcuma longa* is chemically characterized in that it contains a protein fraction with a concentration around 20–30%, measured by the Pierce method, analyzing the protein nitrogen, and a polysaccharide content (ukonan A, B and C) between 3–8%, with no curcuminoids. The procedure for manufacturing *Curcuma longa* extracts is not the object of this invention.

Alternatively, combinations of the two extracts can be used, obtaining hydroalcoholic extracts chemically characterized by the concentration of their markers (concentration of curcuminoids, proteins and polysaccharides).

The content of the markers can be measured by the methods described in the state of the art. The curcuminoids can be quantified by visible-ultraviolet spectrophotometry at 420 nm, the protein fraction can be quantified by the Pierce method, analyzing the protein nitrogen and/or by liquid chromatography and the polysaccharide fraction is quantified by liquid chromatography.

The hydroalcoholic extract of *Curcuma longa* has shown a pharmacological activity greater than curcumin (greater proliferative activity, greater photosensitivisation activity, greater inhibition of cytokine secretion). These results support the view that vegetable extracts are drugs that are different than the molecules responsible for pharmacological activity, because the pharmacodynamics are different (absorption, distribution, action and elimination), and there could be synergic or anti-synergic effects between the different chemical species present in the extract. The hydroalcoholic extract of *Curcuma longa* has shown an antiproliferative activity similar to betametasone-17-valerate. This hydroalcoholic extract showed a significant decrease in the incorporation of 5-bromine-2'-deoxyuridin (BrdU) in the DNA of human keratinocyte cultures between concentrations of 5 $\mu$g/ml and 50 $\mu$g/ml of extract. This effect is similar to that of betametasone-17-valerate.

Both the aqueous extract of *Curcuma* and the hydroalcoholic extract of *Curcuma longa* have inhibited the secretion of cytokine IL-6 and/or IL-8 in human keratinocyte cultures with an activity similar to betametasone-17-valerate. This inhibition is increased after subjecting the cells to ultraviolet A radiation.

The aqueous and hydroalcoholic extracts of *Curcuma* have been seen to inhibit cell proliferation without altering the mitochondrial activity, and the extracts have no effect on protein synthesis. The extract therefore shows cytostatic activity.

On the other hand, the hydroalcoholic extracts show photosensitivisation activity and can therefore be used in proliferative diseases such as psoriasis, vitiligo, lymphomas, mycosis fungoides, etc, instead of psoralens.

In studies carried out on eucaryote cells (human ketinocytes) with *Curcuma longa* extracts, the activated curcumin has been found in the cytoplasm. Therefore the nucleus is free from curcumin and the extract does not interact with the nuclear DNA and the secondary and mutagenic effects produced by psoralens do not appear.

The hydroalcoholic extract (10% curcuminoids, 18% protein fraction, 3% polysaccharides) of *Curcuma* shows a greater photosensitivisation activity after UVA radiation than curcumin.

Therefore, a smaller amount of the drug is best for a greater photosensitivisation activity (lower percentage of BrdU incorporated).

| % incorporation | 80 | 60 | 40 | 20 |
| --- | --- | --- | --- | --- |
| Ng extract | 2000 | 4000 | 5000 | 6000 |
| Ng curcumin equiv | 200 | 400 | 500 | 600 |
| Ng curcumin | 600 | 800 | 1000 | 1200 |

To produce the same level of photosensitivisation as *Curcuma* extracts, doses of 10 ng/ml of psoralen is required, as with this dose toxic and mutagenic effects are produced.

The administration of a cream the active ingredient of which is the aqueous extract of Curcuma longa at 2%, and one tablet a day with 100 mg of aqueous extract with pharmaceutically acceptable excipients has been seen to be clinically effective in different types of psoriasis, and these effects are increased after radiation with ultraviolet A light. There are no side effects, as is the case for corticoids.

22 patients with different types of psoriasis were studied: Guttate, Vulgar, Inverse, Palmo-plantar, Pustular. They were without any psoriasis treatment (retinoids, corticoids, etc.) for 15 days. The cream with aqueous Curcuma extract was then applied and a tablet was administered every 12 days. The cream was tolerated perfectly by all the patients and no patient had to cease treatment because of cutaneous or systemic adverse reactions.

All the patients and all the types of psoriasis responded to this therapy. In the palmo-plantar psoriasis, which does not react to conventional treatments, all the patients responded to the treatment. In the vulgar psoriasis, the plaque was reduced after administration. Fissured and/or ulcerated pustular psoriasis scarred quickly. An antiseptic and drying effect was observed in the inverse psoriasis.

The association of the aqueous Curcuma extract with UVA favoured the product's activity, whitening the lesions after three days of treatment.

The hydroalcoholic (10% curcuminoids, 18% protein fraction, 3% polysaccharides) extract of Curcuma has shown photosensitivisation activity with visible light, inhibiting the percentage of BrdU incorporated into the DNA after radiation with visible light in human keratinocyte cultures.

The administration of a cream in which the active ingredient is the hydroalcoholic extract of Curcuma longa at 2% with pharmaceutically acceptable excipients has been shown to be clinically effective in the different types of psoriasis that did not respond to treatment with corticoids or with PUVA. After 15 days of treatment with the cream with hydroalcoholic extract of Curcuma longa, the erythema, the infiltration and the scaling disappeared. The effects were greater after radiation with visible light and there were no side effects, unlike with the use of psoralens and ultraviolet light.

Curcuma longa extracts (50 mg of alcoholic extract and 50 mg of polar extract of Curcuma longa), equivalent to 10 mg of curcuminoids and 15 mg of proteins and 2 mg of polysaccharides) together with pharmaceutically acceptable excipients, administered for 30 days, 2 tablets a day to 30 healthy individuals (16 men–14 women) aged between 24 and 75, showed a significant reduction in the fibrinogen levels. The values at the end of treatment were between 240–290 mg/dl. After administering the Curcuma extracts, the levels of fibrinogen in plasma fell to standard levels. In other words, Curcuma extracts have no fibrinolitic activity, merely reducing the levels of fibrinogen in individuals with high fibrinogen levels.

Values of 809, 690, 584, 490 mg/dl of fibrinogen became values of 241, 240, 290, 272 mg/dl after the treatment.

Coagulation parameters such as Quick's index, thrombin time, ATPP and prothrombin time did not experience significant changes and the values at the end of treatment were within reference values.

No side effects such as haemorrhages, nausea, vomiting, etc., were not observed. No tablets were observed to be toxic.

The following examples illustrate the invention, but they are not exhaustive to the scope of the invention.

EXAMPLE

Example 1

Variation of Plasmatic Fibrinogen and Coagulation Parameters after Curcuma Intake The effect of Curcuma extracts on fibrinogen and coagulation parameters was studied in a total of 30 healthy individuals (16 men and 14 women) between 24 and 75 years of age with a good state of health.

At time zero blood was extracted from the ulnar vein and plasmatic fibrinogen was determined by the Clauss coagulation method (Clauss A. Acta haemat 1957;17: 237), together with the coagulation parameters.

2 tablets a day were administered for 15 days. After 30 days of treatment the plasmatic fibrinogen and the coagulation parameters were measured once again.

Composition of each tablet:

| | |
|---|---|
| Hydroalcoholic Curcuma extract | 100.0 mg* |
| Microcrystalline cellulose | 490.8 mg |
| Corn starch | 45.0 mg |
| Aerosil | 1.5 mg |
| Primojel | 22.5 mg |
| Encompress | 15.0 mg |
| Magnesium stearate | 10.1 mg |

*Equivalent to no less than 10 mg of curcuminoids, 15 mg of protein fraction and 2 mg of polysaccharides.

Following are the results obtained:

| SEX | FIBRINOGEN T = 0 | FIBRINOGEN T = 30 |
|---|---|---|
| M | 228 | 215 |
| F | 263 | 267 |
| M | 237 | 215 |
| F | 245 | 272 |
| F | 173 | 250 |
| M | 256 | 216 |
| M | 354 | 335 |
| F | 220 | 243 |
| M | 216 | 210 |
| M | 205 | 221 |
| M | 226 | 371 |
| M | 189 | 168 |
| F | 251 | 282 |
| F | 216 | 216 |
| F | 251 | 302 |
| M | 191 | 191 |
| M | 476 | 272 |
| F | 302 | 218 |
| F | 243 | 187 |
| M | 207 | 201 |
| M | 232 | 305 |
| M | 296 | 296 |
| M | 809 | 241 |
| F | 237 | 409 |
| M | 254 | 267 |
| F | 480 | 268 |
| F | 690 | 240 |
| M | 584 | 290 |
| F | 490 | 272 |
| F | 490 | 272 |

Fibrinogen reference values: 150–450 mg/dl.

The *Curcuma* extract normalized pathological fibrinogen values to reference values.

Variation of coagulation parameters after the intake of *Curcuma longa*

| Prothrombin time | | Quick's I | | APTT | | Thrombin time | |
|---|---|---|---|---|---|---|---|
| T = 0 | T = 30 | T = 0 | T = 30 | T = 0 | T = 30 | T = 0 | T = 30 |
| 13.3 | 13.3 | 85.9 | 85.9 | 29.3 | 30.6 | 16.6 | 17.0 |
| 12.3 | 13.5 | 95.7 | 84.2 | 30.9 | 28.1 | 15.9 | 11.0 |
| 13.2 | 13.4 | 86.8 | 85.1 | 29.3 | 31.2 | 17.3 | 15.9 |
| 14.2 | 14.1 | 78.7 | 74.0 | 37.9 | 34.4 | 16.6 | 16.8 |
| 13.8 | 13.6 | 81.7 | 83.4 | 30.7 | 26.5 | 16.6 | 12.0 |
| 13.1 | 14.2 | 87.7 | 78.7 | 31.2 | 33.5 | 16.4 | 16.2 |
| 13.2 | 12.8 | 86.8 | 90.6 | 30.8 | 31.3 | 17.0 | 16.2 |
| 13.3 | 12.8 | 85.9 | 90.6 | 30.1 | 31.4 | 15.9 | 15.9 |
| 13.5 | 14.1 | 84.2 | 79.4 | 30.4 | 30.3 | 16.9 | 16.3 |
| 14.8 | 13.8 | 74.5 | 81.7 | 30.6 | 32.3 | 16.3 | 16.0 |
| 12.9 | 13.7 | 86.6 | 82.5 | 33.9 | 30.0 | 15.9 | 15.8 |
| 14.6 | 13.9 | 75.8 | 80.9 | 34.7 | 31.8 | 17.2 | 16.3 |
| 13.5 | 12.3 | 84.2 | 95.7 | 36.8 | 30.2 | 17.1 | 16.4 |
| 13.7 | 13.7 | 82.5 | 82.5 | 29.5 | 29.5 | 16.7 | 16.7 |
| 13.0 | 13.5 | 88.7 | 84.2 | 31.2 | 29.8 | 17.3 | 16.7 |
| 14.4 | 14.4 | 77.2 | 77.2 | 33.3 | 33.3 | 17.1 | 17.1 |
| 12.0 | 14.9 | 99.1 | 73.8 | 31.3 | 29.3 | 15.9 | 15.5 |
| 14.0 | 13.9 | 80.2 | 80.9 | 29.9 | 33.2 | 16.8 | 15.2 |
| 12.9 | 14.3 | 89.6 | 77.9 | 30.3 | 32.3 | 15.9 | 16.3 |
| 14.3 | 13.9 | 77.9 | 80.9 | 35.2 | 32.8 | 17.3 | 17.3 |
| 13.8 | 12.2 | 81.7 | 96.9 | 30.6 | 28.9 | 16.2 | 16.7 |
| 12.6 | 12.6 | 92.6 | 92.6 | 33.0 | 33.0 | 15.9 | 15.9 |
| 13.7 | 13.5 | 82.5 | 84.2 | 29.1 | 29.1 | 16.1 | 17.0 |
| 13.1 | 11.6 | 87.7 | 100 | 30.2 | 30.5 | 16.2 | 14.0 |
| 13.0 | 12.4 | 88.7 | 94.7 | 28.7 | 28.9 | 16.2 | 16.2 |
| 14.8 | 13.8 | 89.6 | 90.9 | 32.9 | 29.9 | 16.1 | 15.9 |
| 15.2 | 14.0 | 83.2 | 89.8 | 31.6 | 30.1 | 17.2 | 14.9 |
| 13.9 | 13.9 | 86.8 | 100 | 34.2 | 32.4 | 15.4 | 16.0 |
| 14.6 | 12.8 | 70.9 | 88.8 | 30.8 | 28.8 | 15.9 | 16.3 |
| 13.8 | 14.1 | 84.8 | 90.4 | 33.7 | 30.0 | 16.1 | 14.8 |

Reference values:
Prothrombin time: 10–20 seconds
Thrombin time: 10–20 seconds
Quick's Index: 75–100
APTT: 28–40 seconds.

After treatment, all the values are within the reference values.

Example 2

Variation of the Apolipoprotein B/Alipoprotein A Quotient after the Intake of *Curcuma* Tablets The effect of *Curcuma* extracts on apolipoproteins A-I and B was studied in a total of 13 healthy individuals of between 24 and 75 years of age, with a state of health.

At time zero blood was extracted from the ulnar and apolipoproteins A-I and B were determined nephelometrically and their quotient was then calculated. After 15 days of treatment, as in example 1, apolipoproteins A-I and B were analysed once again.

| Apo B | | Apo A | | ApoB/ApoA | |
|---|---|---|---|---|---|
| T = 0 | T = 30 | T = 0 | T = 30 | T = 0 | T = 30 |
| 100 | 120 | 104 | 100 | 1.04 | 0.83 |
| 120 | 160 | 141 | 110 | 1.17 | 0.68 |
| 157 | 172 | 136 | 126 | 0.86 | 0.73 |
| 130 | 141 | 96 | 90 | 0.73 | 0.63 |
| 146 | 160 | 65 | 60 | 0.44 | 0.38 |
| 155 | 166 | 70 | 53 | 0.46 | 0.32 |
| 90 | 136 | 101 | 82 | 1.10 | 0.59 |
| 125 | 164 | 99 | 74 | 0.79 | 0.45 |
| 110 | 151 | 86 | 76 | 0.78 | 0.50 |
| 160 | 179 | 109 | 88 | 0.68 | 0.49 |
| 99 | 133 | 102 | 90 | 1.03 | 0.67 |
| 104 | 141 | 116 | 103 | 1.10 | 0.73 |

After the intake of *Curcuma longa* extract we observe a significant decreasing trend for the ApoB/ApoA quotient.

Example 3

Effect of Aqueous *Curcuma* Extract on Psoriasis

Quantitative composition of the cream:

| Aqueous Curcuma extract* | 2% |
|---|---|
| Greasy phase | 27% |
| Emulgents | 47% |
| Humectants | 20% |
| Preservatives | 1% |
| pH adjusters | 1% |
| Water | sq |

*Content in proteins no less than 15%, content in polysaccharides no less than 4%.

22 patients diagnosed with psoriasis were studied, distributed by age and sex.

| Sex | Age | Type of psoriasis |
|---|---|---|
| F | 12 | Guttate |
| F | 22 | Vulgar |
| F | 37 | Palmo-plantar |
| M | 24 | Vulgar |
| M | 48 | Vulgar |
| F | 51 | Inverse |
| F | 27 | Palmo-plantar |
| M | 19 | Vulgar |
| M | 57 | Palmo-plantar |
| M | 61 | Inverse |
| F | 46 | Palmo-plantar |
| M | 6 | Pustular |
| M | 16 | Vulgar |
| F | 32 | Vulgar |
| F | 39 | Pustular |
| F | 41 | Vulgar |
| M | 31 | Palmo-plantar |
| F | 13 | Guttate |
| F | 3 | Vulgar |
| F | 51 | Vulgar |
| F | 60 | Inverse |
| F | 19 | Palmo plantar |

Criteria for inclusion:
Patients clinically or histologically diagnosed with psoriasis.
They had no other disease.
They did not receive treatment for psoriasis.
Protocol:
The 22 patients went for 15 days without treatment of any kind, emollients, corticoids, retinoids, fatty acids.
Patients were instructed to apply the formula 3 times a day with a light massage and take 1 tablet every 12 hours.
Results:
All the patients tolerated the treatment well. The cream presented no irritation or contact reaction.
The cases of guttate psoriasis evolved in the same way. Their lesions were not very scaly but very erythematous. After 7 days of treatment there were no scaled and the erythema was minimal. After 14 days the lesions were not visible. There were no residual pigmentation lesions.
4 of the 6 cases of psoriasis palmo-plantar had the palms more evidently affected, with scaly lesions and significant fissuration. After 7 days of treatment the fissuration, painful for the patients, had disappeared and been replaced by an erythematous lesion with badly defined borders with practically no scales. After 14 days, the lesions had been reduced to a slightly erythematous macula on skin with normal characteristics. The plantar lesions presented an important hyperkeratosis with fissuration and were more resistant to treatment, obtaining results after 14 days, with scarred fissures.
In the two patients with pustular psoriasis, the lesions scarred after a week of treatment and the scales disappeared after 14 days of treatment.
In the patients with inverse psoriasis, the lesions were slightly scaly and intensively erythematous with an eroded surface. Cultures were prepared and they were contaminated with Candidas. After 7 days of treatment, scale shedding had ceased and the erythema was reduced. After 14 days of treatment only a slightly erythematous macula was observed.
The most studied case was vulgar psoriasis, because it represented the largest number of patients. The lesions in the trunk area presented considerable infiltration and peripheral scale shedding. Hyperkeratosis was predominant on the articulations. After 7 days of treatment the infiltration and the erythema was drastically reduced. After 14 days reaction was positive on both the trunk and the articulations, and very slightly erythematous lesions were observed on the trunk and slightly scale-shedding lesions on elbows and knees.
In patients with palmo-plantar psoriasis treated with PUVA, the fissures and scale shedding disappeared 72 hours after treatment. In patients with vulgar psoriasis treated with PUVA, the lesions showed no infiltration and scale shedding after 2 sessions.

Example 4

Figure 1:
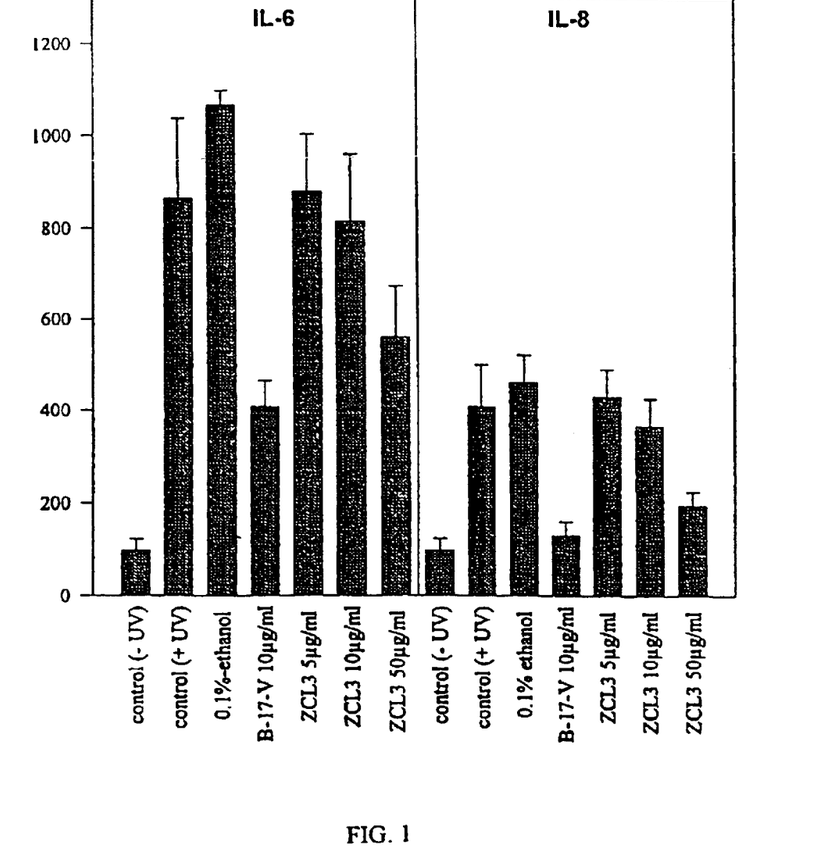
FIG. 1—Inhibition of the secretion of IL-6 and IL-8 after ultraviolet light radiation of aqueous Curcuma extract (ZCL3) and betametasone-17-valerate (B-17-V).
Figure 2:
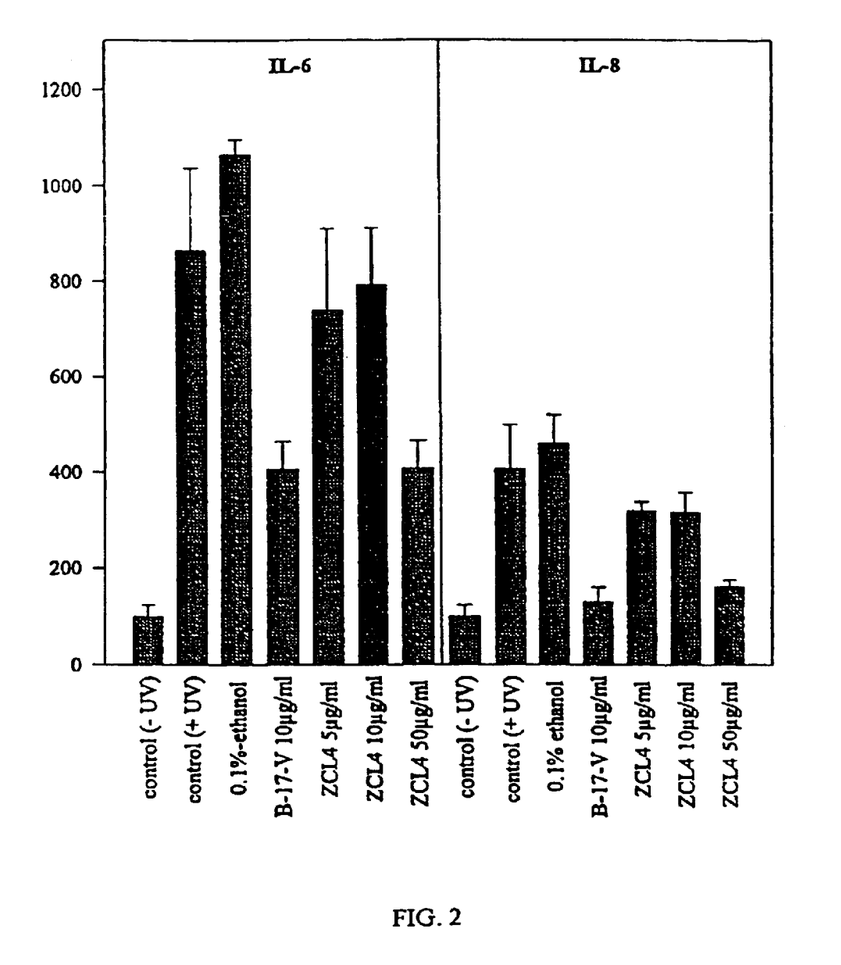
FIG. 2—Inhibition of the secretion of IL-6 and IL-8 after ultraviolet light radiation of hydroalcoholic Curcuma extract (ZCL4) and betametasone-17-valerate (B-17-V).

Effects of *Curcuma longa* Extracts on the Secretion of Interleukins IL-6 and IL-8 in Human Keratinocyte Cultures Culture of the HaCat line:
The HaCat line is an immortalized line of normal human keratinocytes. These cells grow in a culture medium consisting of Hanks liquid to which 5% of foetal bovine serum and 2% of penicillin-streptomycin is added at 37° C. in a $CO_2$ atmosphere.
Determination of the interleukins.
After 48 hours of incubation with or without radiation, the supernadant of the cultures is taken to measure the IL-6 and IL-8 using an ELISA test kit. The minimum detection for each test is 3.13 pg/ml for the IL-6 and 31.0 pg/ml for the IL-8.
Cell radiation.
The cells were radiated by an UVA/UVB lamp with a UVA range of 340–390 nm and a UVB range of 290–310, with no UVC. The radiation dose was 150 mJ/cm$^2$. To avoid toxic products from the culture media from forming, PBS free calcium and magnesium ions were changed before radiation.
Results:
The hydroalcoholic and aqueous *Curcuma* extracts, at doses of 50 µg/ml, inhibited the secretion of interleukins IL-6 and IL-8 after radiation with UVB light in a similar way to betametasone-17-valerate.
FIGS. 1, 2

Example 5

Effect of *Curcuma longa* Extracts on the Incorporation of BrdU in the DNA of Human Keratinocytes Culture of the HaCat line:
The HaCat line is an immortalized line of normal human keratinocytes. These cells grow in a culture medium consisting of Hanks liquid to which 5% of foetal bovine serum and 2% of penicillin-streptomycin is added at 37° C. in a $CO_2$ atmosphere.
Incorporation of BrdU:
To determine the replication rate, the cells were grown in microplates at a density of $2*10^4$ cells per matrix. After 24 hours of treatment the media was renewed and the cultures were incubated for 24 hours at 37° C. with different concentrations of the extracts and betametasone-17-valerate with a concentration of 10 µg/ml. Parallel controls were carried out with the solvent (ethanol 0.1%). The incorporation of BrdU was determined with the ELISA test.

Figure 3:
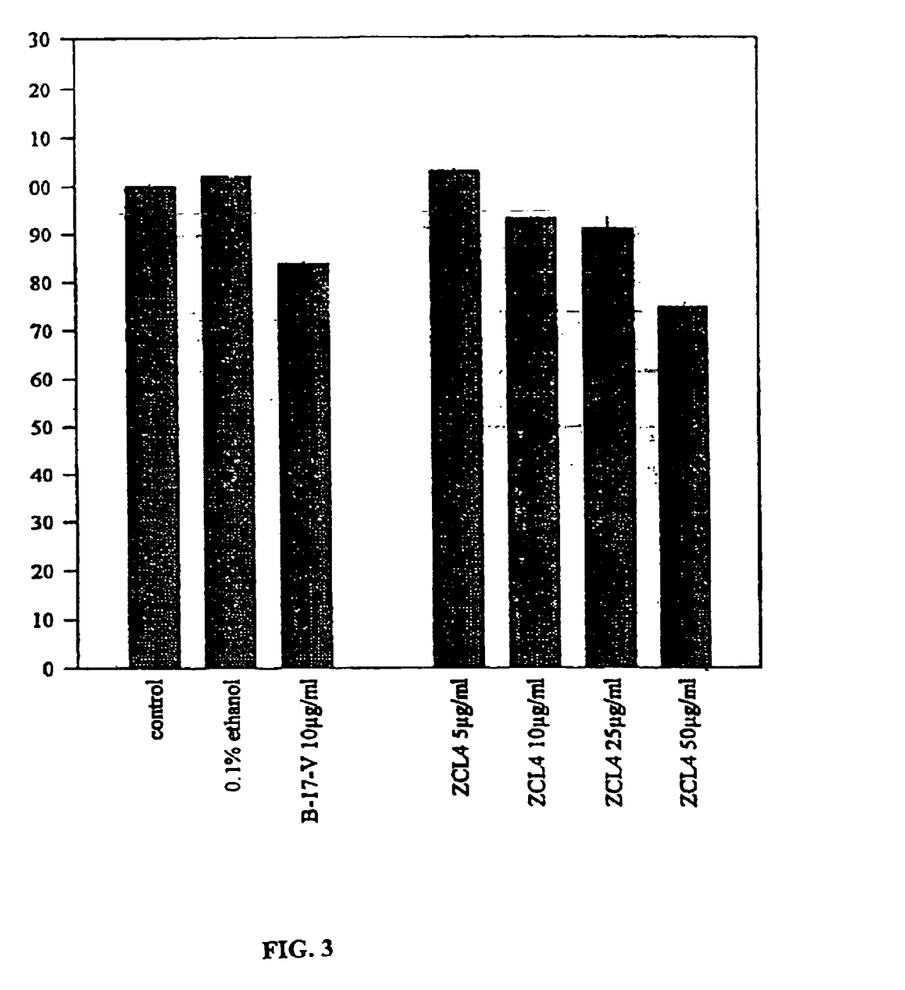
FIG. 3—Incorporation of BrdU of hydroalcoholic Curcuma extract (ZCL4) and betametasone-17-valerate (B-17-V).
Figure 4:
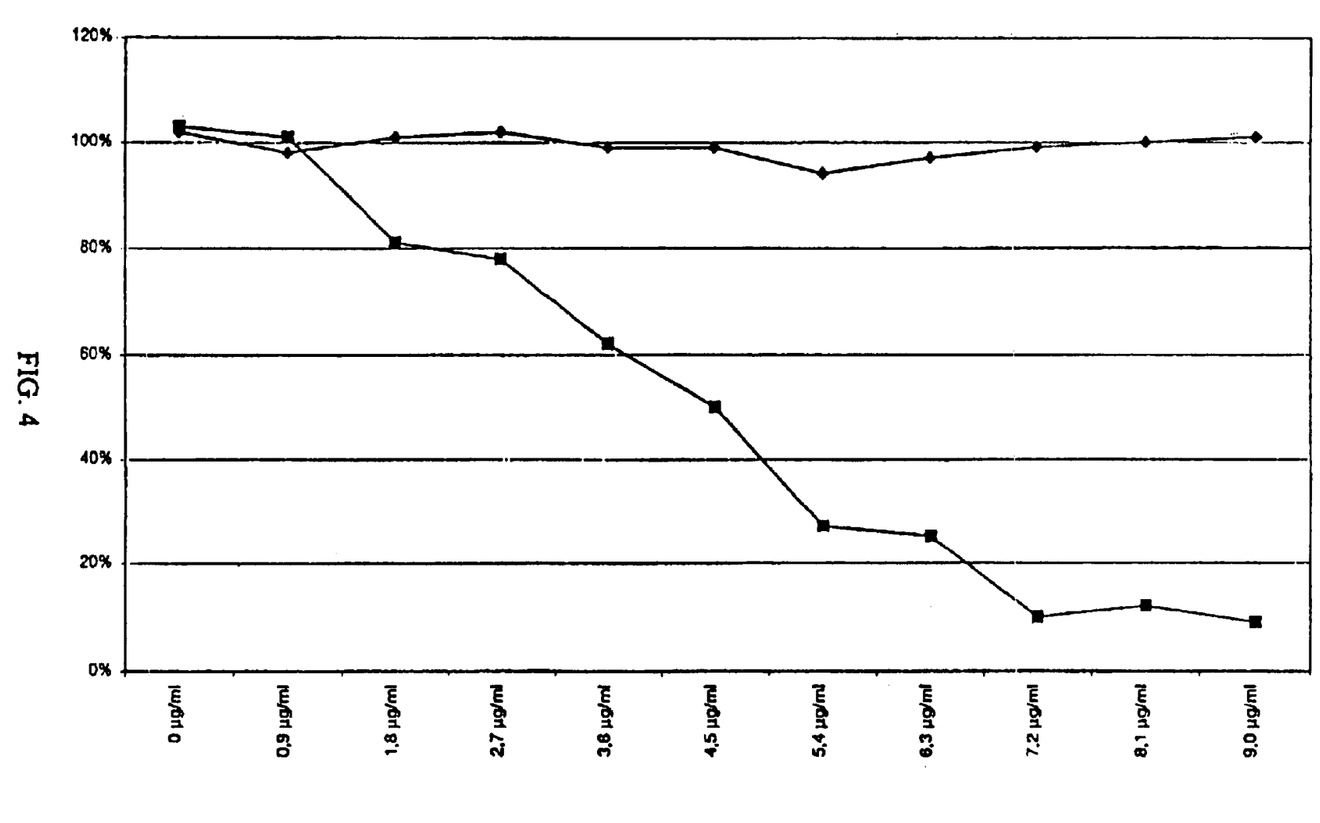
FIG. 4—Effect of aqueous Curcuma extract (ZCL3) on the incorporation of BrdU in the DNA after UV radiation. Photosensitive capacity.
Figure 5:
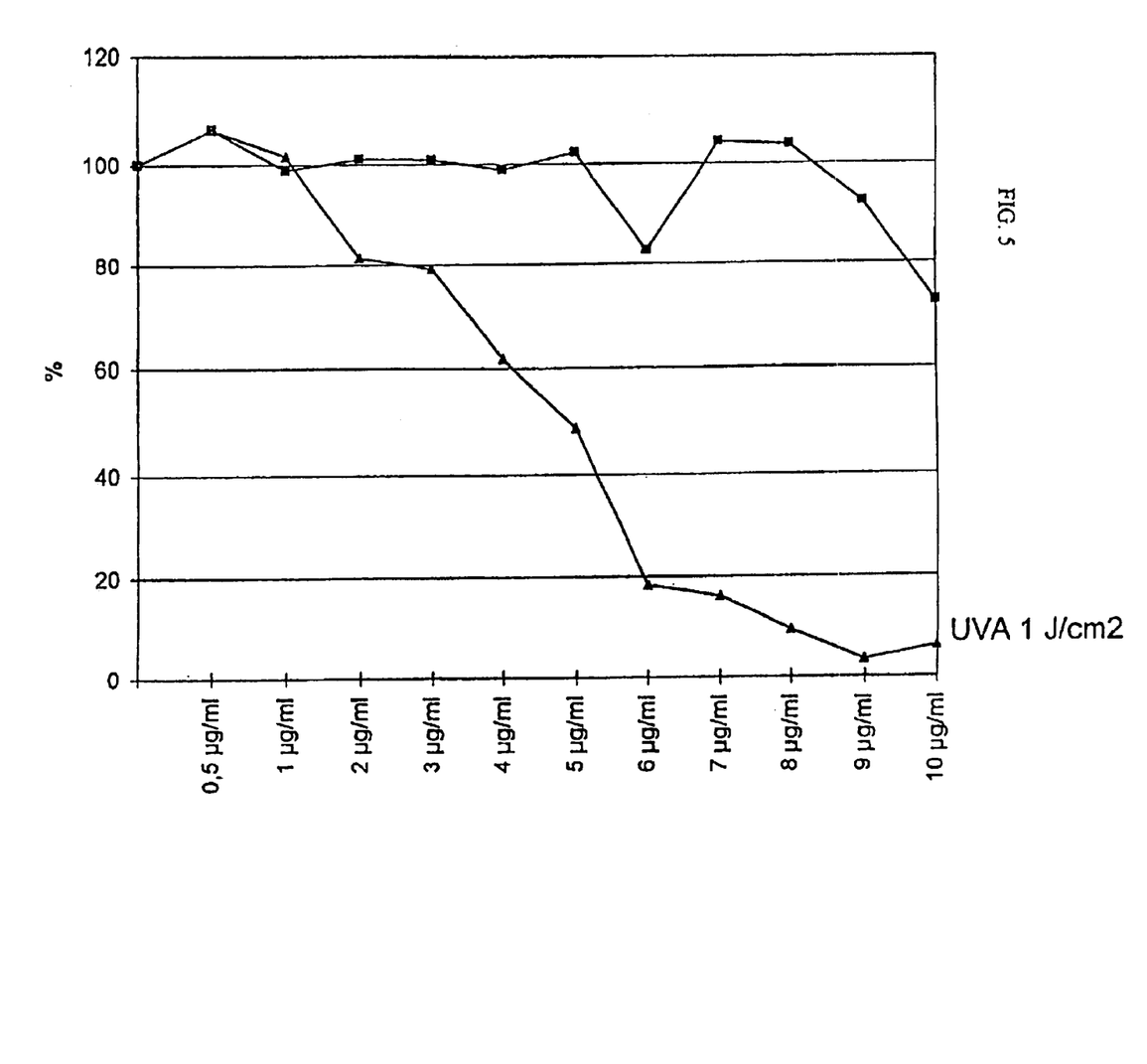
FIG. 5—Effect of hydroalcoholic Curcuma extract (ZCL4) on the incorporation of BrdU in the DNA after UV radiation. Photosensitive capacity.
Figure 6:
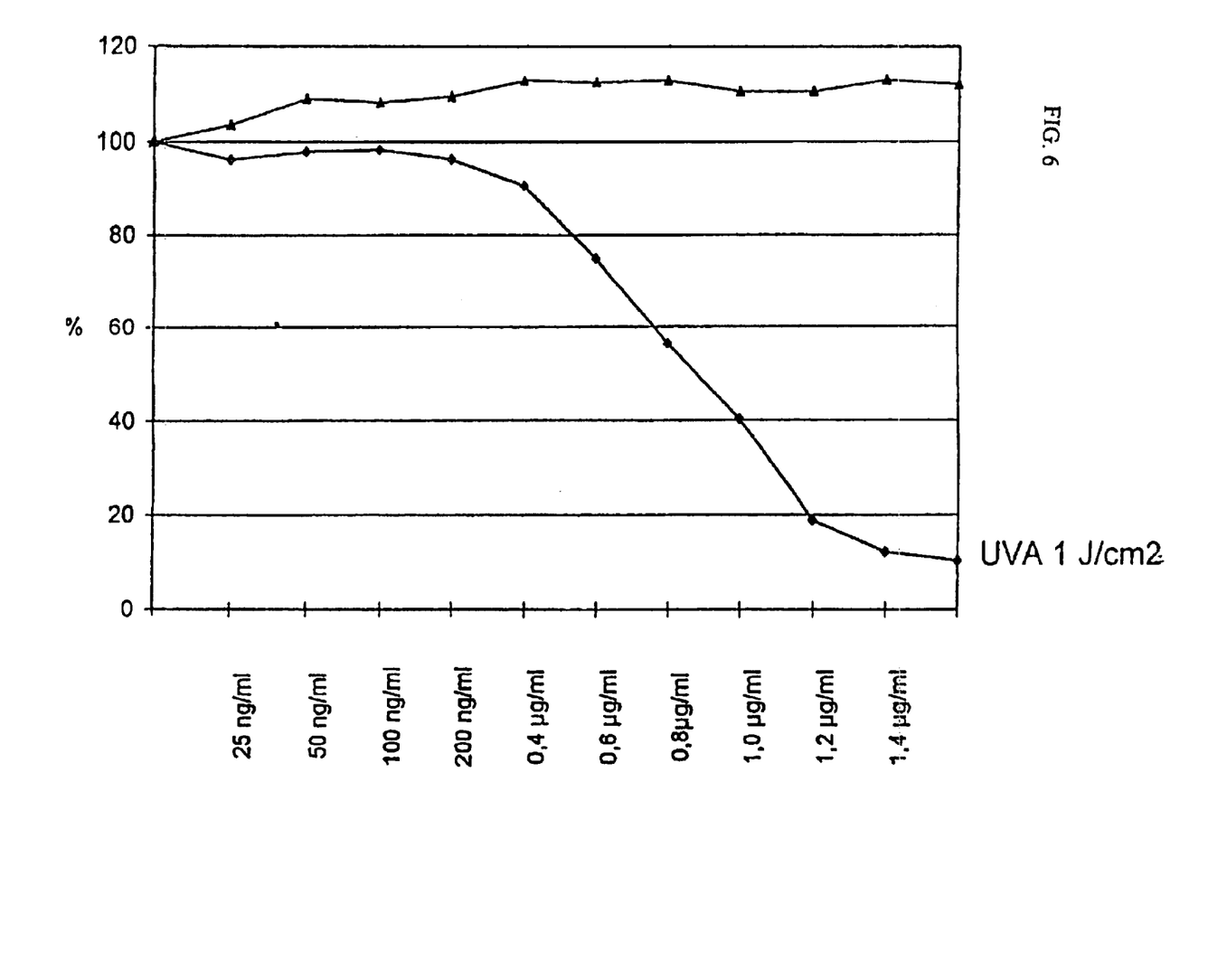
FIG. 6—Effect of curcumin on the incorporation of BrdU in the DNA after UV radiation. Photosensitive capacity.
Figure 7:
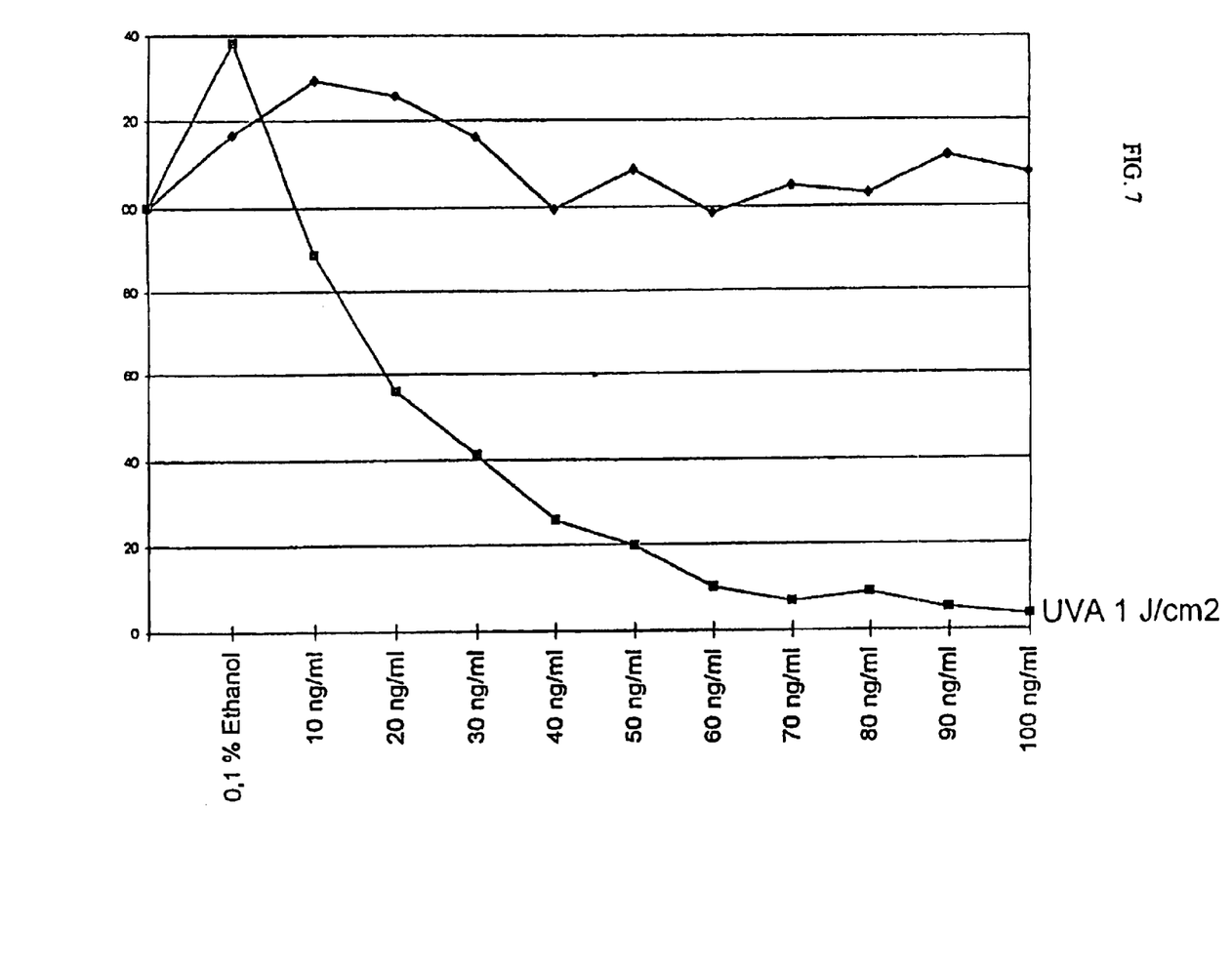
FIG. 7—Effect of psoralen on the incorporation of BrdU in the DNA after UV radiation. Photosensitive capacity.

Results:

The incubation of the cells with 50 μg/ml of hydroalcoholic extract leads to a significant decrease in the incorporation with BrdU. The hydroalcoholic extract, a combination of the aqueous and alcoholic extract of *Curcuma longa*, showed an antiproliferative activity similar to betametasone-17-valerate. FIG. 3.

Example 6

Effect of *Curcuma longa* Extracts on the Incorporation of BrdU in the DNA of Human Keratinocytes after Radiation with Ultraviolet Light Culture of the HaCat line The HaCat line is an immortalized line of normal human keratinocytes. These cells grow in a culture medium consisting of Hanks liquid to which 5% of foetal bovine serum and 2% of penicillin-streptomycin is added at 37° C. in a $CO_2$ atmosphere.

Incorporation of BrdU:

To determine the replication rate, the cells were grown in microplates at a density of $2*10^4$ cells per matrix. After 24 hours of treatment, the media was renewed and the cultures were incubated for 24 hours at 37° C. with different concentrations of the extracts and different concentrations of the curcumin and psoralen. Parallel controls were carried out with the solvent (ethanol 0.1%). The incorporation of BrdU was determined with the ELISA test.

The cells were radiated with UVA light at an intensity of 1 $J/cm^2$ and the incorporation of BrdU was then analysed.

Results:

The hydroalcoholic extract of *Curcuma longa* with 10% curcuminoids, 18% proteins and 3% polysaccharide fraction, showed a photosensitivisation activity greater than curcumin after radiation with UVA light, that is less percentage of incorporation.

Aqueous *Curcuma longa* extract has photosensitivisation properties.

To produce the same level of photosensitivisation as *Curcuma* extracts, toxic doses of psoralen (10 ng/ml) have to be used. FIGS. 4, 5, 6, 7.

Example 7

Effect of the Hydroalcoholic Extracts of *Curcuma longa* on Psoriasis with Visible Radiation Quantitative composition of the pharmaceutical product:

| | | |
|---|---|---|
| Hydroalcoholic Curcuma extract* | 2% | |
| Greasy phase | 27% | |
| Emulgents | 47% | |
| Humectants | 20% | |
| Preservatives | 1% | |
| pH adjusters | 1% | |
| Water | sq | |

*Equivalent to 10% of curcuminoids, 18% of proteins.

8 patients who were affected and diagnosed with and treated for different types of psoriasis: Guttate, Vulgar, Inverse and Palmo-plantar. The previous treatment consisted of the application of corticoid creams, PUVA sessions (around 14 sessions per patient) and in some cases retinoid therapy. The distribution of the patients by sex, age and type of psoriasis was as follows.

| Age | Sex | Type of psoriasis |
|---|---|---|
| 9 | Female | Palmar psoriasis |
| 6 | Female | Guttate psoriasis |
| 31 | Male | Vulgar psoriasis |
| 46 | Female | Vulgar psoriasis |
| 19 | Female | Palmo-plantar psoriasis |
| 56 | Female | Vulgar and palmo-plantar psoriasis |
| 14 | Female | Guttate psoriasis |
| 28 | Male | Inverse psoriasis |

The cream with the hydroalcoholic extract was applied to the lesions and after 10 minutes the patients were radiated with a 440 nanometer lamp for three minutes. Sessions were weekly. The erythema, the infiltration and the scale shedding was evaluated after 48 hours, 5 days and 15 days.

The results obtained were:

| Type of psoriasis | Erythema | Infiltration | Scale shed |
|---|---|---|---|
| Day 0 | | | |
| Palmar psoriasis | ++ | +++ | +++ |
| Guttate psoriasis | ++ | +++ | ++ |
| Vulgar psoriasis | ++ | ++ | +++ |
| Palmo-plantar psoriasis | + | +++ | +++ |
| Inverse psoriasis | +++ | ++ | + |
| Day 2 | | | |
| Palmar psoriasis | ++ | ++ | ++ |
| Guttate psoriasis | ++ | ++ | + |
| Vulgar psoriasis | + | ++ | +++ |
| Palmo-plantar psoriasis | + | + | ++ |
| Inverse psoriasis | ++ | ++ | + |
| Day 5 | | | |
| Palmar psoriasis | ++ | + | + |
| Guttate psoriasis | + | + | − |
| Vulgar psoriasis | + | + | + |
| Palmo-plantar psoriasis | + | − | ++ |
| Inverse psoriasis | − | + | − |
| Day 15 | | | |
| Palmar psoriasis | + | − | − |
| Guttate psoriasis | + | − | − |
| Vulgar psoriasis | − | − | + |
| Palmo-plantar psoriasis | − | − | + |
| Inverse psoriasis | − | − | − |

+++intense
++moderate
+slight
−negative

An improvement was observed in the erythema, infiltration and skin shedding after treatment with *Curcuma longa* extract and visible light.

Example 8

Effect of *Curcuma longa* Extracts on the Incorporation of BrdU in the DNA of Human Keratinocytes after Radiation with Visible Light Culture of the HaCat line The HaCat line is an immortalized line of normal human keratinocytes. These cells grow in a culture medium consisting of Hanks liquid to which 5% of foetal bovine serum and 2% of penicillin-streptomycin is added at 37° C. in a $CO_2$ atmosphere.

Incorporation of BrdU:

To determine the replication rate, the cells were grown in microplates at a density of $2*10^4$ cells per matrix. After 24 hours of treatment, the media was renewed and the cultures were incubated for 24 hours at 37° C. with different concentrations of the extracts and different concentrations of the curcumin and psoralen. Parallel controls were carried out with the solvent (ethanol 0.1%). The incorporation of BrdU was determined with the ELISA test.

The cells were radiated with visible light using an actinium lamp with a spectrum of 400–550 nm (maximum at 450 nm)

Figure 8:
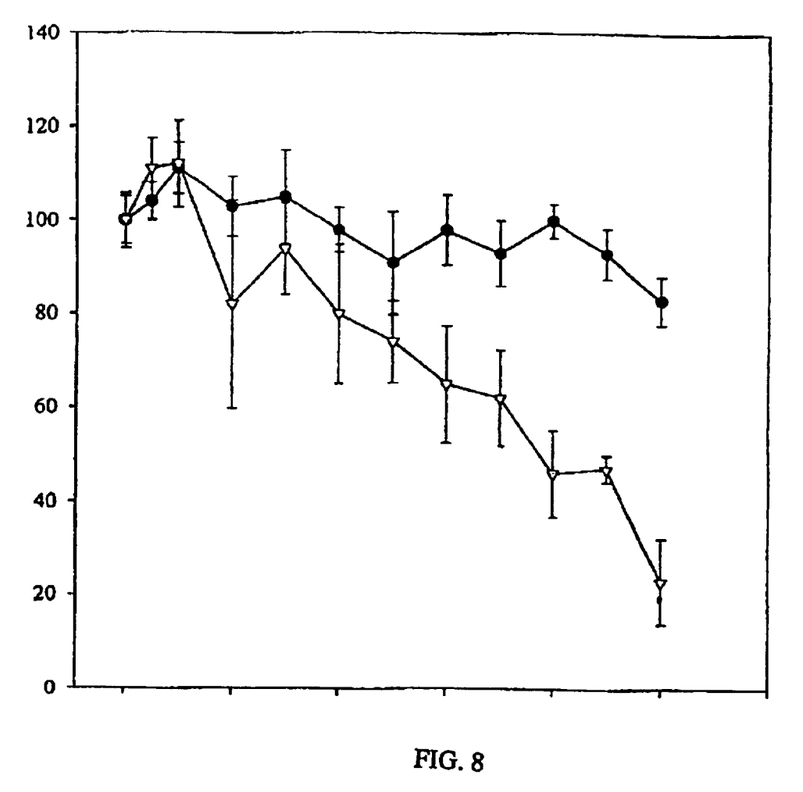
FIG. 8—Effect of the hydroalcoholic extract of Curcuma longa on the incorporation of BrdU in the DNA of human keratinocytes with visible light radiation (450 nm) and without radiation, with the concentration in µg/ml of extract represented on abscissas and the percentage of BrdU incorporation on ordinates. Photosensitivisation capacity with visible light.

Results:

The hydroalcoholic extract of *Curcuma longa* with 10% of curcuminoids, 18% of proteins and 3% of polysaccharide fraction showed a decrease in DNA synthesis. The maximum inhibition of BrdU incorporation was at concentrations of 10 μg/ml of extract. FIG. 8.

What is claimed:

1. A method for reducing plasma fibrinogen in a human having a pathological value of plasma fibrinogen, the method comprising administering to said human an effective amount of a pharmaceutical composition comprising at least one compound present in *Curcuma* rhizomes.

2. The method according to claim 1, wherein said at least one compound is present in the form of a *Curcuma* extract.

3. The method according to claim 1, wherein the pharmaceutical composition comprises curcuminoids.

4. The method according to claim 1, wherein said at least compound is obtained by extracting *Curcuma* rhizomes using a solubilizing lipophilic compound.

5. The method according to claim 4, wherein said lipophilic compound is ethanol.

6. The method according to claim 4, wherein said at least one compound is in the form of an aqueous extract of *Curcuma*.

7. The method according to claim 1, wherein said method results in a reduction of Apolipoprotein B/Apolipoprotein A-1 quotient in said human.

8. The method according to claim 1, wherein said *Curcuma* rhizomes are *Curcuma longa* rhizomes.

9. The method according to claim 1, wherein said human has cardiovascular disease.

10. The method of claim 1, wherein said pathological value of plasma fibrinogen is greater than about 450 mg/dl.

* * * * *